(12) United States Patent
LaBoisse

(10) Patent No.: US 6,210,965 B1
(45) Date of Patent: Apr. 3, 2001

(54) CELL CULTURE PROCESS AND MEDIUM, CELLULAR COMPOSITION OBTAINED AND ITS APPLICATION AS PRODUCTION SYSTEM AND STUDY MODEL

(75) Inventor: Christian LaBoisse, Nantes (FR)

(73) Assignee: Universite de Nantes, Nantes Cedex (FR)

( * ) Notice: Subject to any disclaimer, the term of this patent is extended or adjusted under 35 U.S.C. 154(b) by 0 days.

(21) Appl. No.: 09/171,364

(22) PCT Filed: Apr. 15, 1997

(86) PCT No.: PCT/FR97/00668
§ 371 Date: Nov. 10, 1998
§ 102(e) Date: Nov. 10, 1998

(87) PCT Pub. No.: WO97/39109
PCT Pub. Date: Oct. 23, 1997

(30) Foreign Application Priority Data

Apr. 16, 1996 (FR) .................................... 96 04709
Dec. 24, 1996 (FR) .................................... 96 15947

(51) Int. Cl.$^7$ .................................... C12N 5/00
(52) U.S. Cl. .................... 435/325; 435/383; 435/384; 435/404; 435/405
(58) Field of Search .................... 435/325, 404, 435/383, 384, 405

(56) References Cited

U.S. PATENT DOCUMENTS

| 4,254,226 | * | 3/1981 | Eisinger et al. | 435/404 |
| 4,456,687 | * | 6/1984 | Green | 435/404 |
| 5,712,163 | * | 1/1998 | Parenteau et al. | 435/205 |

* cited by examiner

Primary Examiner—Leon B. Lankford, Jr.
(74) Attorney, Agent, or Firm—Young & Thompson

(57) ABSTRACT

The invention relates, inter alia, to a process for in vitro culture of any cells whatsoever, of human or animal origin. The process's characterizing feature is that it involves at least a stage of transitional incubation of the said cells, isolated in an incubation medium in the form of a solution whose constituents are chosen in such a manner that the final calcic concentration of the solution is between [0–1 mM], and preferably [0–100 $\mu$M], to induce rapid and massive adherence of the isolated cells to any given support in contact with the said incubation medium. Applications to gastrointestinal epithelium cell culture and vaccine production in fermenter units.

6 Claims, 3 Drawing Sheets

CELL CULTURE PROCESS AND MEDIUM, CELLULAR COMPOSITION OBTAINED AND ITS APPLICATION AS PRODUCTION SYSTEM AND STUDY MODEL

The present invention relates to a process and in vitro culture medium for cells, such as primary normal or tumoral cells or cellular lines, of human or animal origin, a cellular composition based on gastro-intestinal epithelial cells and a system for the production of bioactive molecules and/or of m-RNA including such a system as well as a study model constituted by said composition.

The culture of any cells of human or animal origin always comprises a step of adherence of these cells to a support which again can be anything. This adherence step is necessary to obtain a correct survival rate of the cells whilst ensuring maintenance of their specialized functions. Conversely, an absence of adherence of the cells to a support gives rise to rapid death of said cells.

This adherence step further poses a certain number of problems that must be resolved, in particular for certain primary, normal or tumoral cells, particularly the fragile ones. Thus, it is not always known until now to maintain in primary culture pure populations of gastro-intestinal epithelial cells, whilst, in the same manner, it is known that the intestinal epithelium constitutes an extraordinary sense of bioactive peptides which could have high interest for industry such as pharmaceutical industries.

The methods described until now to maintain the culture of such populations were essentially based on the reconstitution of extra-cellular matrices and/or the utilization of predetermined media supplemented by various proteins and growth factors. Certain authors have essayed the reconstitution in vitro of the three-dimensional structure of the intestinal crypt on an endothelial "feeder-layer". However, all these methods are seen to be inoperative in practice because of the very low adherence rate and, hence, low viability of the cells undergoing culture, by the absence of reproducibility of the results, by the too great complexity of the methods used and by the absence of maintenance of the difference functions of said cells. These methods have been used for certain normal tumoral cells which at present have the same problems.

Similarly, cell culture, in particular of cellular lines, on an industrial scale, is also very dependent on the step of adherence for different reasons from those given above. Thus, for example, optimization of the culture conditions by acceleration of the adherence and by mass adherence of the cells, constitutes a determining factor for the improvement of the output of mass cultures carried out on microballs in a fermenter, for example. As a result, the adherence must be effected under conditions such that there is obtained a very high rate of adherence of the cells to any support and this in a very short time. However, until now, the culture media used requires several hours to cause adherence of the cells to a support and moreover contain animal proteins which are in danger of being damaged in this type of medium because of the risks of contamination by virus and/or by a pathogenic agent of the prion type of the cells. The step of adherence is thus a long step, difficult and risky, in particular for the production of vaccines.

A first object of the invention is thus to provide an in vitro culture process for any type of cells which permits causing them rapidly to adhere in mass to any support to ensure their survival.

Another object of the invention is to provide an incubation medium for said simple cells to be produced and adapted to induce rapid inherence in mass of the cells to any support, this medium permitting moreover to obtain pure populations of cells which have never previously been able to be obtained.

Another object of the present invention is to provide an incubation medium for said cells chemically predetermined to be exempt from elements, in particular proteins, risking contamination of the cells undergoing culture by infectious agents of a viral nature or the like which could be carried by said elements.

Another object of the invention is to provide a cellular composition of a new type of which the cells, because of their adherence in mass to a support, can be maintained in culture under good conditions for a time up to several days.

Another object of the invention is to provide a system for the production by the epithelium of biologically active molecules and/or of ARNm coding for these molecules, these molecules being adapted to be constituted by new and inventive molecules.

Another object of the present invention is again to provide a study model in vitro of epithelial intestinal cells which permits, because of the incorporation in this model of a pure population of normal intestinal epithelial cells, an in vitro study of said cells, of the manner of regulation of their proliferation and their differentiation, of the expression of their specialized functions and of the metabolism and the toxicity of various substances which can be absorbed, particularly medicines and foodstuffs, under conditions near those which would be obtained in the case of in vivo studies.

To this end, the invention has for its object a process for the in vitro culture of cells, such as primary normal or tumoral cells and/or cellular lines, of human or animal origin, characterized in that it comprises at least one step of transitional incubation of said cells, preferably isolated, in an incubation medium in the form of a solution whose constituents are so selected that the final calcic concentration of the solution is comprised in the ratio 0–1 mM, preferably 0–100 $\mu$M, to give rise to rapid adherence in mass of said isolated cells to any support in contact with said incubation medium.

According to a preferred embodiment of the invention, the cells, once having adhered to their support, are cultivated in a culture medium whose calcic concentration is progressively increased to a predetermined value adapted to ensure the survival of the cells and to maintain their specialized functions.

The invention also relates to an incubation medium for cells, such that the primary normal or tumoral cells and/or the cellular lines, of human or animal origin, particularly for the practice of the previously-recited culture process, characterized in that it is present in the form of a solution whose constituents, particularly the salts, are selected such that the final calcic concentration of the solution is comprised in the rate 0–1 mM, preferably 0–100 $\mu$M, to give rise to the mass adherence of the incubated cells in their medium to any support in contact with said incubation medium.

The interest of such an incubation medium is its simplicity of production, its composition free from contaminants, such as proteins, in particular proteins of animal origin.

The invention also has for its object a cellular composition of a new type, characterized in that it is constituted of a pure population of gastro-intestinal epithelial cells adhering to a support, the adherence to said support having been obtained by transitional incubation of a primoculture of gastro-intestinal epithelial cells isolated from mammals in an incubation medium in the form of a solution whose constituents are so selected that the final calcic concentration of the solution of the incubation medium is comprised in the range 0–100 mM, preferably 0 to 100 µM.

When it is cultivated in these suitable culture media, this cellular composition can be used on the one hand as a system for in vitro production by the gastro-intestinal epithelium, of biologically active molecules such as growth factors, repair factors and/or ARNm coding for said molecules, on the other hand as an in vitro study model of the behavior of the intestinal epithelial cells particularly in fields such as pharmacotoxicology, immunology, in particular to assist in the production of vaccines, and genetic therapy.

The invention will be better understood from the reading of the following description of one embodiment, with reference to the accompanying drawings, in which.

Figure 1:
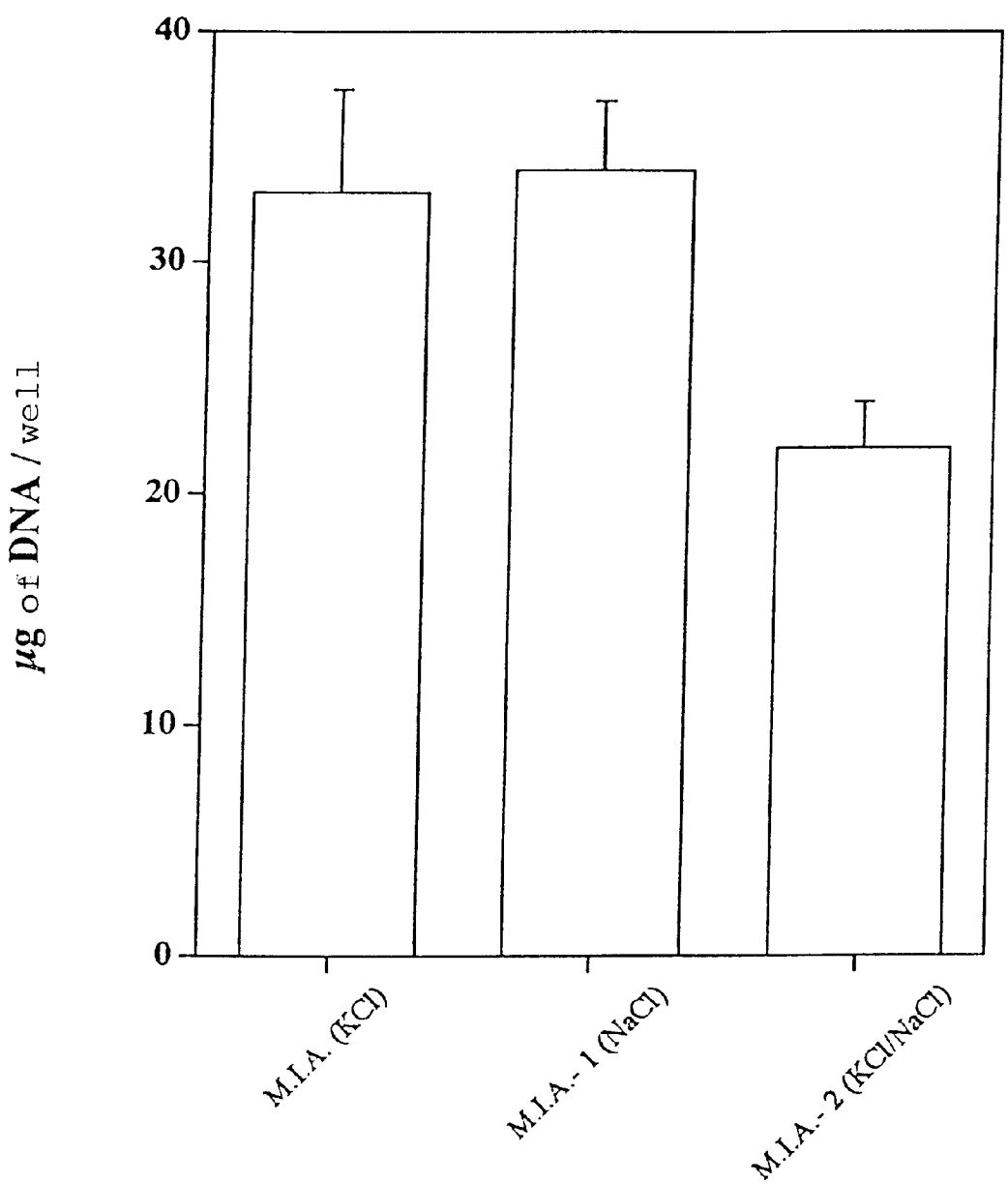
FIG. 1 shows in graphical form the influence of the composition, in particular of its cationic concentration, of the incubation medium, on the adherence of cells.

The in vitro culture process for cells will be more particularly described hereafter in connection with the culture of gastrointestinal epithelial cells. However, all types of primary normal or tumoral cells or of cellular lines can be used in the form of a cellular suspension to permit practice of the process.

The in vitro culture process of gastro-intestinal epithelial primary cells described hereafter will be broken down into four steps of which only steps 2 and 3 are characteristic of the present invention.

Step 1 consists in obtaining suspensions of gastrointestinal epithelial cells isolated from mammals, in particular adult men. The choice of adult human cells is preferred by reasons of the destination of these cells (pharmacotoxicological studies, immunological studies, etc.). This step requires a removal of the organ or organ fragment of the mammal and, in the case of men, a piece of resection obtained in the course of a surgical intervention. The isolation of these gastrointestinal epithelial cells is carried out from said removed organ or organ fragment. This step 1 uses conventional protocols widely described in the literature.

Step 2 is characterized by the seeding of these cellular suspensions obtained in step 1 in a incubation medium characteristic of the invention. This incubation medium permits the cells to adhere or to attach in mass and rapidly, to a support. This adherence step is indispensable to maintain said cells live and to maintain their essential functions.

Step 3 consists in placing a culture of said cells thus adhered to their support into a culture medium whose calcic concentration is progressively increased to permit the cells to survive under conditions permitting the maintenance of their specialized functions. This characteristic is important to permit an ultimate study of the behavior of said cells. The culture medium which is the basis of step 3 can be a so-called standard culture medium used for the culture of cells.

Step 4 consists in modifying the culture medium, if desired by addition of elements, or by replacing this culture medium with another culture medium to permit either the production intracellularly or extracellularly by the cells of particular biologically active molecules, either for carrying out tests of the behavior of said cells with respect to elements introduced into said culture media or directly in the cells. This step 4 can consist in carrying out tests already carried out for example on transformed gastro-intestinal epithelial culture lines to verify the results which were obtained with such cellular lines.

There will now be described in detail steps 1 through 4 of this process. The primary cells or first explantation cells, useful for practice of the invention, are obtained from organs or fragments of organs of the gastrointestinal system, such as small intestine, the colon, the stomach, removed from mammals. More particularly, in adult males, the removal is carried out on pieces of surgical resection of healthy mucous membranes distant from a tumor.

The removal of mucous membranes and isolation of gastro-intestinal epithelial cells from such a piece are well-known non-enzymatic disassociation techniques, particularly described by Ahnen and colleagues (Am. J. Physiol. 254, G 610–G 621-1988). The operational protocol described above is thus cited only by way of example.

After opening and rinsing the colectomy piece, mucous membrane fragments are removed and immediately placed in a PBS solution (made by GIBCO-BRL) free from calcium and magnesium but containing antibiotics and sodium citrate (27 mM). These magnets are rinsed twice in this solution, called solution 1. Solution 1, supplemented with EDTA 1 mM, is injected below the epithelium, then the mucous membrane is totally immersed in this solution. Incubation is carried out on a shaking plate for 20 min. at ambient temperature. This promotes the disassociation of the epithelium from the rest of the mucous membrane. The mucous membrane is then delicately scraped with the soft edge of a scalpel blade. The cellular suspension is filtered on bolt cloth with a porosity of about 250 µm. Filtrate is centrifuged at 1300 rpm for 10 minutes. The supernatant is eliminated and the cellular residue obtained is freed from erythrocytes by gentle suction with a Pasteur pipette. This cellular residue is again washed with a medium which, preferably, is the incubation medium which will be described hereinafter. This washing is followed by another centrifugation. The supernatant is again eliminated. The residue from centrifugation thus obtained is constituted of so-called primary gastrointestinal epithelial cells. These cells can have a very low level of contamination by non-epithelial cells.

The cellular residue thus obtained permits the practice of step 2, the so-called adherence step of the cells to a support, which is the step characteristic of the present invention. The cellular residue obtained is returned into suspension in an incubation medium, itself placed in contact with any support. By any support, it is meant any conventional support used for cellular culture. Thus, by way of example, the cellular suspension can be distributed either into petri dishes, or into wells of multiwell culture plates (96 well plate produced by Nunc or Falcon), or into glass or plastic culture flasks. There should be noted here one of the primary interests of this process. Thus, it is not necessary to give the support a pretreatment with adherence proteins or with a serum, contrary to the culture processes used until now. There is thus avoided any risk of contamination of the cultivated cells, particularly by a viral or bacterial agent. It is no longer necessary to combine to this seeding the presence of other cells.

The cells are left to incubate for about 30 minutes at 37° C. in a $CO_2$ atmosphere. This time is the mean time necessary for maximum adherence of the cells to the support. However, as a function of the quality of the cells of the cellular residue used, it will be noted that said isolated cells can be incubated in said incubation medium for a predetermined period of time generally comprised in the range of 5 to 60 minutes, to obtain a yield of adherence of cells to the support which can be nearly 100%. Under certain circumstances, the adherence is extremely rapid and requires only 5 to 10 minutes of incubation in said medium. In other cases, several tens of minutes are required to permit obtaining an adherence output permitting optimum use of the final steps of the process. The yield values obtained vary between 60 and 100% with a mean of 90±8%. In all cases, however, this incubation step is a transitional step which serves for the transition between the removal step and the obtention of the cellular residue, and the culturing step.

Several culture media having all the same characteristics can be used in this step 2. The incubation medium must in all cases be present in the form of a solution whose constituents are selected such that the final calcic concentration of the solution is comprised in the range of 0–100 mM, preferably 0–100 µM, to give rise to rapid adherence and in mass of said isolated cells on the support in contact with said incubation medium. The preferred incubation medium is a medium with controlled pH and osmolarity which is present in the form of a solution comprised at least one nutrient element and one or several salts so chosen that at least one of the cations is present in the solution at a concentration at least equal to 50% of the final cationic concentration of said solution. The inventors believe that this characteristic of the culture medium permits introducing a condition of membranous depolarization of the cells which promotes the adherence of these latter to the support. Thus, by way of example, this incubation medium comprises at least, in addition to a nutrient element such as glucose and/or creatine and if desired an antioxidant such as taurine, at least one or several salts such as potassium or sodium salts, the said salt or salts being selected in the manner described below.

An example of preferred composition of said incubation medium can be as follows:
KCl: 30–90 mM
K-glutamate: 1–10 mM
$KH_2PO_4$: 10–50 mM
$MgSO_4$: 1–10 mM
$CaCl_2$: 0–0.1 mM
EGTA: 0–1 mM
creatine: 1–10 mM
taurine: 1–30 mM
glucose: 5–30 mM
Hepes: 10 mM
pH adjusted to 7.2 with KOH.

This medium will be called a medium inducing adherence (M.I.A.) (KCl). In this case, the potassium cation constitutes the predominant cationic species.

There could also be considered a composition for the incubation medium as follows:
NaCl: 30–90 mM
Na-glutamate: 1–10 mM
$NaH_2PO_4$: 10–50 mM
$MgSO_4$: 1–10 mM
$CaCl_2$: 0–0.1 mM
EGTA: 0–1 mM
creatine: 1–10 mM
taurine: 1–30 mM
glucose: 5–30 mM
Hepes: 10 mM
pH adjusted to 7.2 with KOH.

This medium will be called a medium inducing adherence-1 (M.I.A.-1) (NaCl). In this case, the sodium cation constitutes the predominant cationic species.

There could also be used an incubation medium whose composition is as follows:

KCl: 15–45 mM
NaCl: 15–45 mM
$KH_2PO_4$: 10–50 mM
$MgSO_4$: 1–10 mM
$CaCl_2$: 0–0.1 mM
EGTA: 0–1 mM
creatine: 1–10 mM
taurine: 1–30 mM
glucose: 5–30 mM
Hepes: 10 mM
pH adjusted to 7.2 with KOH.

This medium will be called a medium inducing adherence-2 (M.I.A.-2) (KCl/NaCl).

FIG. 1 shows the effectiveness of these media to promote adherence of the cells to their support. This graph has been established from normal human colon epithelial cells which have been seeded at equal density in plates of 6 wells (Costar) in the media M.I.A. (KCl), M.I.A.-1 (NaCl), M.I.A.-2 (KCl/NaCl) and left to incubate for 30 minutes. After incubation, the non-adhering cells were eliminated by washing and the adhering cells were quantified by dosing with DNA in the wells by the Burton Method modified by Taylor and Colleagues. (Journal of Steroid Biochemistry 20 (1984) 1083–1088). It will thus be noted that the monocationic composition of the incubation medium gives rise to a higher yield of adherence of the cells to their support.

Figure 2:
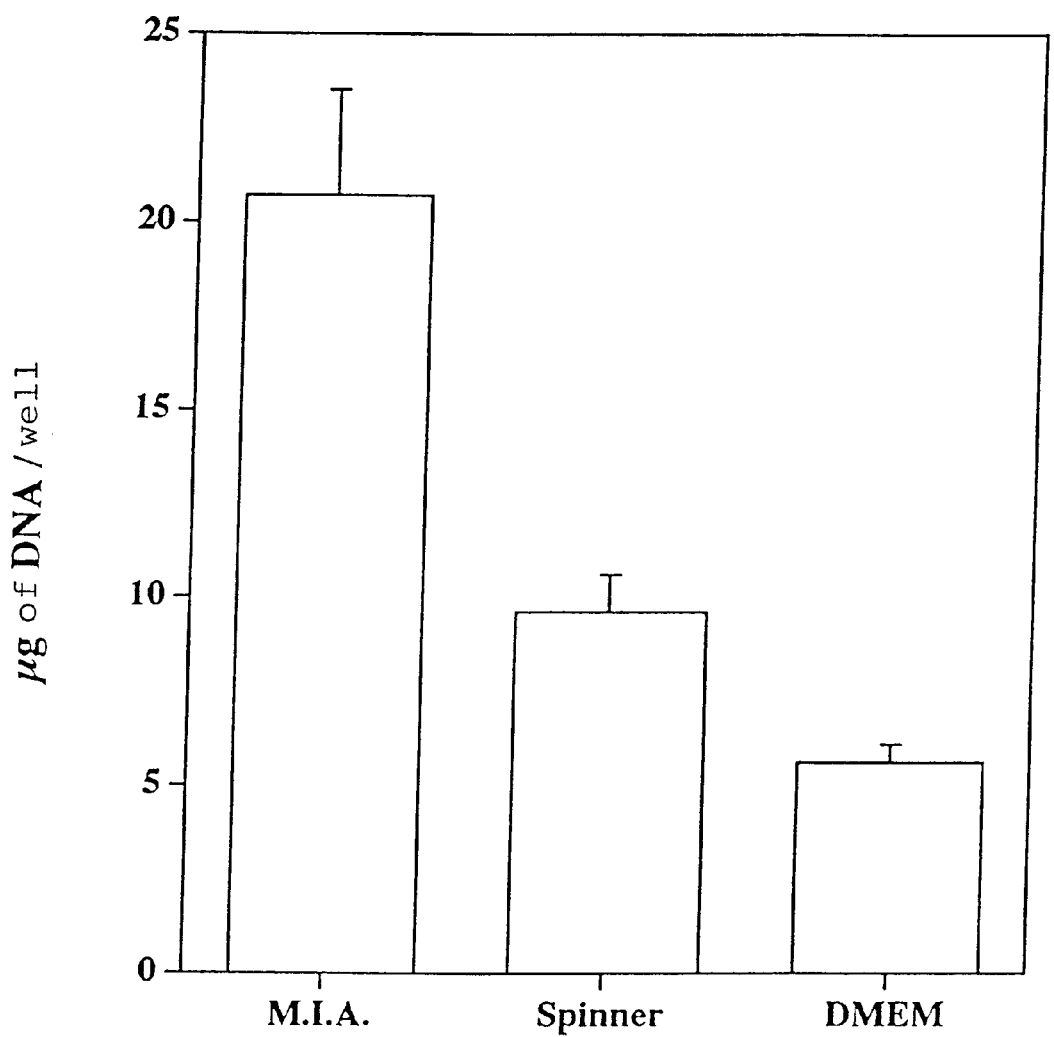
FIG. 2 shows in graphical form a comparative test of the efficacy of induction of adherence of the cells to a support with three different incubation media and FIG. 3 is a curve which shows, in the course of time, the quantity of Interleukine-8 secreted by the normal human intestinal epithelial cells treated or not with a pathogenic agent.

Another experiment shown in graphical form (FIG. 2) has been carried out so as to test the efficacy of the different incubation media on the adherence of the gastrointestinal epithelial cells, including standard culture media. Thus, the normal human colon epithelial cells have been seeded with equal density on 6 well plates (Costar) in the following media: DMEM (standard culture medium produced by Gibco-BRL), Spinner-MEM (standard culture medium without calcium produced by Gibco-BRL) and the M.I.A. (KCl) medium as described above. After incubation of 30 minutes, the non-adhering cells were eliminated by washing and the adhering cells were quantified by dosage with DNA into the wells in a manner analogous to that described above. FIG. 2 shows clearly that the M.I.A. (KCl) medium is particularly efficacious in terms of adherence of the cells to their support. The DMEM medium did not itself permit using the final steps because of the low concentration of the cells adhering to their support. Thus, this low adherence gives rise to low reproducibility of the system. The spinner-MEM medium free from calcium could if desired be used as an incubation medium.

The cells thus obtained can, once adhered to their support, be cultured in a culture medium suitable to ensure the survival of the cells and to maintain their specialized functions. Thus, if this incubation needs to be prolonged for a period of time greater than that described above, there will soon be noted a high mortality rate for said cells. It is thus necessary, once the adherence of the cells to their support is effected, to replace the incubation medium by a suitable culture medium. The inventors have also discovered that, if the cells, once adhered to their support, are cultivated in a culture medium whose extracellular calcic concentration is high, the mortality of the cells is very high. It has also been noted that, if the adherence were carried out under bad conditions, for example with an incubation medium such as the spinner or DMEM medium, these cells will not retain, as a result, when cultured in a suitable culture medium, all of their functions. Because of this, a complete study of these cells is not possible. As a result, to obtain for example cells by culture of which the characteristics are the nearest to normal living cells, these cells, once adhered to their support, are cultivated in a culture medium whose extracellular calcic concentration is progressively increased to a predetermined value adapted to ensure the survival of the cells and to maintain their specialized functions.

Thus, by way of example, once the adherence of the cells is obtained, the M.I.A. (KCl) medium can be eliminated and replaced by a culture medium, called medium A, whose base is the Spinner-MEM medium (produced by GIBCO-BRL) containing also 0.08 mM $CaCl_2$+insulin ($5 \cdot 10^{-8}$M)+ transferrin (10 μg/ml)+EGF (epithelial growth factor) (5 ng/ml). After incubation for 30 minutes at 37° C. in a $CO_2$ atmosphere, a third of the volume of this medium is removed and replaced by the DMEM medium (produced by GIBCO-BRL), while maintaining constant the concentration of insulin, EGF and transferrin. The object of these successive changes is to increase progressively the calcic concentration of the solution to a final extracellular calcic concentration of about 1 mM. Obviously, this final extracellular calcic concentration can be greater than this value. The extracellular calcic concentration, in most of the culture media, is of the order of 1.8 mM.

In general, the culture medium adapted for the survival of said cells is a medium whose nutritive base comprises, in addition to nutritive elements and one or several salts, at least insulin and/or transferrin and/or choleric toxin and/or epithelial growth factor E.G.F. and/or pituitary extracts and/or dexamethasone and/or selenium and/or serum albumins. The composition of this medium can vary infinitely as a function of the destination of the cells thus cultivated. The cellular composition thus obtained is constituted by a pure population of gastro-intestinal epithelial cells adhered to a support.

This culture process therefore has both the advantage of permitting the survival under good conditions of a large number of gastro-intestinal cells and also to obtain a pure population of these cells. Thus, by way of example, there is obtained an output of adherence of the order of 90% and there is thus obtained cellular concentrations of $10^6$ cells, a figure never obtained until now. This facilitates the performance of step 4. The cells thus concentrated can be maintained in the culture medium for several days and they can lend itself to various operations which are the object of step 4.

Step 4 can take place in various forms as a function of the choice of the user. Thus, the user can decide to use the cellular composition obtained as a system for the production in vitro of biologically active molecules and/or of M-RNA. Thus, by way of example, the pure population of gastrointestinal epithelial cells adhered to a support is cultivated in one or several suitable culture media and is used as an in vitro production system by the gastro-intestinal epithelium of biologically active molecules and/or of m-RN. By biologically active molecules, there is meant particularly growth factors and distribution factors. Thus, as has already been pointed out above, the epithelium constitutes an extraordinary source of bioactive peptides, such as for example peptides with antibacterial activity (defensines), peptides involved in autorepair of the mucous membranes (TGFβ, peptides with a trefoil structure), peptides regulating the epithelial secretions (guanyline) and finally regulating agents for the local immune system (cytokines). The cellular composition can thus be used as a system for production of molecules so as to permit the extraction of said molecules thus produced in the culture medium and their ultimate purification. It is thus also possible, thanks to this cellular composition, to use a process for obtaining biologically active molecules which is characterized by a culture of said cellular composition in a suitable culture medium, such as the medium described above, for a suitable time, then to extract said molecules from the culture medium and purify them.

The same use can also permit the obtention of ARNm which are extracts of said cells. Such a process for obtaining specific ARNm's of the intestinal epithelium is characterized by a step of culturing the cellular composition in a suitable medium, then by a step of extraction of said ARN's from the cells by well-known techniques.

Figure 3:
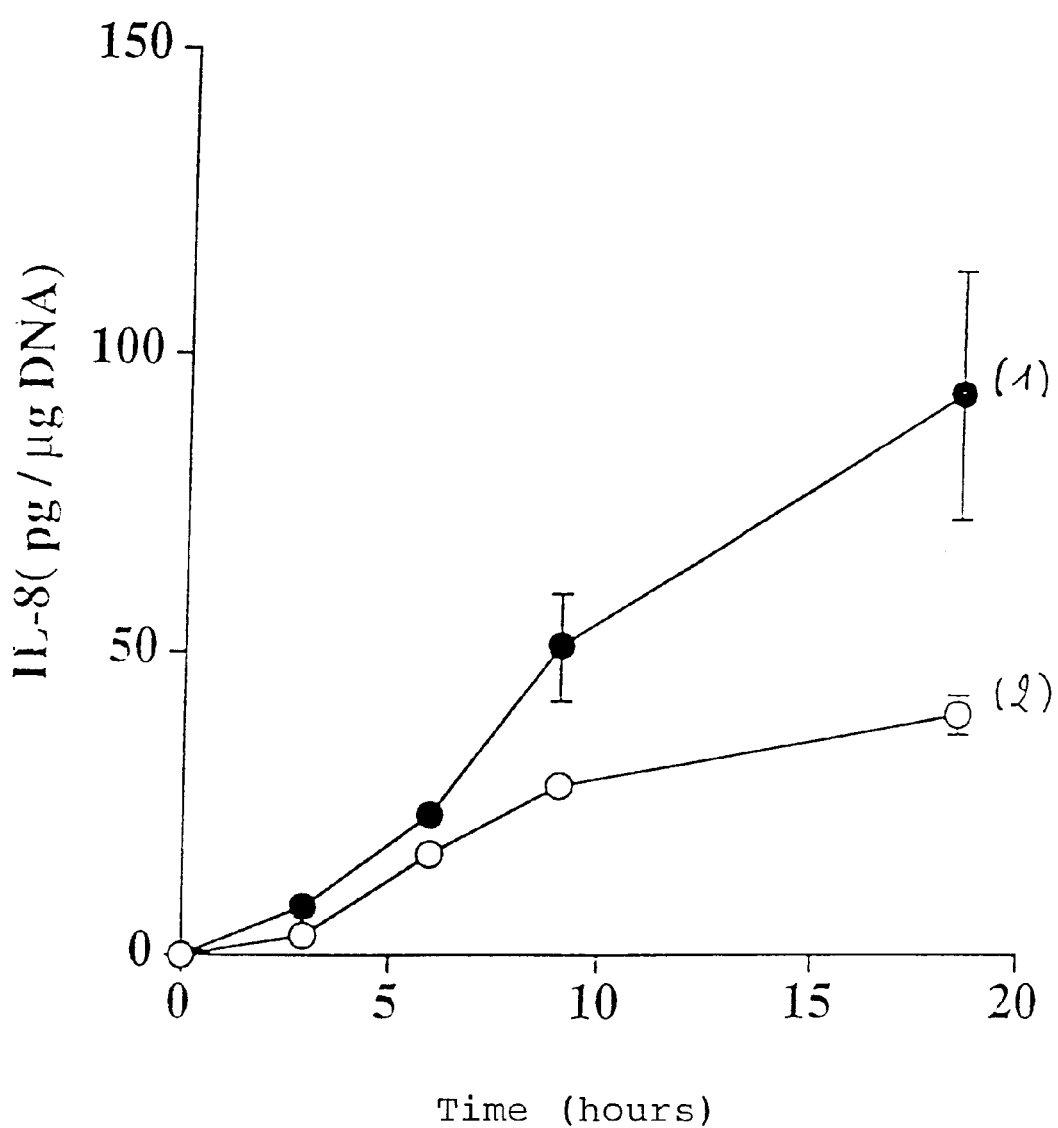

Thus, by way of example, FIG. 3 shows the production of cytokine (Interleukine-8) by normal human intestinal epithelial cells obtained according to steps 1 to 3 described above, these so-called epithelial cells having been cultivated in a culture medium such as the medium described above in the presence (curve 1) or in the absence (curve 2) of a pathogenic agent.

The pathogenic agent introduced into this culture medium permits inducing a production of Interleukine-8 significantly higher than that of untreated cells.

It will therefore be seen now to be possible to produce new molecules from cellular compositions obtained by the practice of the invention by adapting the culture media to each molecule before being produced.

This cellular composition, cultivated in one or several suitable culture media, can also be used for the production of an in vitro study model of the behavior of said cells, particularly in the field of pharmacotoxicology, of immunology, in particular to assist in the production of vaccines, and for genetic therapy. This is of great interest, in particular when the cells are intestinal epithelial cells.

In the case in which the culture process is more particularly adapted to cellular lines cultivated in a fermenter on any supports, such as microballs, the essentially steps of the culture process can be broken down as follows:

seeding the incubation medium, for example the (M.I.A.) (KCl) medium described above, in the fermenter with cells of the line to be cultivated, agitation for about 30 minutes at a temperature of about 37° C., emptying the fermenter and replacing the incubation medium by any culture medium, the cultivated cells being themselves adhered to the microballs disposed within the fermenter.

What is claimed is:

1. In a process for the in vitro culture of cells of human or animal origin, comprising a primary culturing step of culturing said cells in a culture medium adapted to ensure the survival of the cells and to maintain their specialized functions, the improvement comprising, prior to said primary culturing step, performing a preliminary incubation of said cells in an incubation medium different from said culture medium, for a duration of 5–60 minutes, said incubation medium being free of proteins and having a final calcium concentration in t he range of 0–100 μM, said preliminary incubation occurring in the presence of a solid support that is untreated by adherence proteins or serum, said preliminary incubation causing rapid adherence of said cells to said support.

2. The process according to claim 1, wherein, during said primary culturing step, the culture medium is altered such that its calcium concentration is progressively increased.

3. The process according to claim 1, wherein the incubation medium is of controlled pH and osmolarity and is a solution comprising at least one nutritive element, EGTA, and at least one salt selected such that at least one of the cations of the at least one salt is present in the solution at a concentration at lest equal to 50% of the final cationic concentration of said solution.

4. The process according to claim 1, wherein the incubation medium has the following composition:

KCl: 30–90 mM
K-glutamate: 1–10 mM
$KH_2PO_4$: 10–50 mM
$MgSO_4$: 1–10 mM
$CaCl_2$: 0–100 $\mu$M
EGTA: 0–1 mM
creatine: 1–10 mM
taurine: 1–30 mM
glucose: 5–30 mM
Hepes: 10 mM
pH adjusted to 7.2 with KOH.

5. The process according to claim 1, wherein the incubation medium has the following composition:

NaCl: 30–90 mM
Na-glutamate: 1–10 mM
$NaH_2PO_4$: 10–50 mM
$MgSO_4$: 1–10 mM
$CaCl_2$: 0–100 $\mu$M
EGTA: 0–1 mM
creatine: 1–10 mM
taurine: 1–30 mM
glucose: 5–30 mM
Hepes: 10 mM
pH adjusted to 7.2 with KOH.

6. The process according to claim 1, wherein said cells are selected such that said primary culturing step produces a pure population of gastro-intestinal epithelial cells adhered in mass to a support untreated with adherence proteins or serum.

* * * * *